(12) United States Patent
Simula et al.

(10) Patent No.: US 10,576,907 B2
(45) Date of Patent: Mar. 3, 2020

(54) REMOTE SCANNING AND DETECTION APPARATUS AND METHOD

(71) Applicant: GSE TECHNOLOGIES, LLC, Houghton, MI (US)

(72) Inventors: Glen Raymond Simula, Hancock, MI (US); Gary Bryan Howard, Smithfield, MI (US)

(73) Assignee: GSE TECHNOLOGIES, LLC, Houghton, MI (US)

( * ) Notice: Subject to any disclaimer, the term of this patent is extended or adjusted under 35 U.S.C. 154(b) by 35 days.

(21) Appl. No.: 15/196,826

(22) Filed: Jun. 29, 2016

(65) Prior Publication Data

US 2016/0350907 A1 Dec. 1, 2016

Related U.S. Application Data

(63) Continuation-in-part of application No. 14/708,428, filed on May 11, 2015.

(Continued)

(51) Int. Cl.

| | |
|---|---|
| *G06T 7/00* | (2017.01) |
| *H04N 5/225* | (2006.01) |
| *B60R 11/04* | (2006.01) |
| *G01S 17/08* | (2006.01) |
| *H04N 5/33* | (2006.01) |
| *G01S 13/88* | (2006.01) |
| *G01S 19/13* | (2010.01) |
| *G01N 33/42* | (2006.01) |

(Continued)

(52) U.S. Cl.
CPC ............ *B60R 11/04* (2013.01); *G01N 33/42* (2013.01); *G01S 13/885* (2013.01); *G01S 17/08* (2013.01); *G01S 19/13* (2013.01); *B60R 2011/004* (2013.01); *G01N 21/8803* (2013.01); *G01N 21/8851* (2013.01); *G01N 25/72* (2013.01)

(58) Field of Classification Search
CPC .... H04N 5/332; H04N 5/2253; G02S 13/885; G01S 19/13; G01S 17/08; B60R 11/04; G06T 2207/30184; G06T 2207/10016; G06T 2207/10048
USPC ......................................................... 348/128
See application file for complete search history.

(56) References Cited

U.S. PATENT DOCUMENTS

| | | |
|---|---|---|
| 4,690,553 A | 9/1987 | Fukazimu et al. |
| 4,910,592 A | 3/1990 | Shroy, Jr. et al. |

(Continued)

*Primary Examiner* — Hee-Yong Kim
(74) *Attorney, Agent, or Firm* — Brooks Kushman P.C.

(57) ABSTRACT

A surface scanning apparatus attached to a movable highway vehicle, mobile equipment or a drone (collectively, "platform") that passes over a substrate, at least some of the features of which are to be sensed and characterized. The apparatus includes a variously adaptable, complete, and ready to operate packaged kit including configured sensor suites with components selected from the group consisting of a visual scanning sensor; an infra-red scanning sensor; a ground-penetrating radar unit; a laser range finder for sensing elevation of the apparatus above the substrate; a distance sensor for measuring displacement of the apparatus from a point of origin; a position sensing unit for determining a position of the apparatus; a simultaneous trigger mechanism; a structural boom assembly attached to the platform; and a processor for digitally processing measurements and signals collected by one or more of the group of components.

12 Claims, 2 Drawing Sheets

Related U.S. Application Data

(60) Provisional application No. 61/992,472, filed on May 13, 2014.

(51) Int. Cl.
*G01N 21/88* (2006.01)
*G01N 25/72* (2006.01)
*B60R 11/00* (2006.01)

(56) References Cited

U.S. PATENT DOCUMENTS

| | | | |
|---|---|---|---|
| 4,910,593 A | 3/1990 | Weil | |
| 5,563,608 A * | 10/1996 | Tachita | G01C 21/30 342/357.28 |
| 5,790,243 A | 8/1998 | Herr | |
| 7,697,727 B2 | 4/2010 | Xu et al. | |
| 8,803,977 B2 | 8/2014 | Uchima et al. | |
| 2006/0061485 A1 | 3/2006 | Doherty et al. | |
| 2010/0100275 A1* | 4/2010 | Mian | G01M 17/013 701/31.4 |
| 2010/0290703 A1* | 11/2010 | Sim | G06T 5/008 382/172 |
| 2012/0173150 A1 | 7/2012 | Romero et al. | |
| 2012/0218411 A1 | 8/2012 | Wu et al. | |
| 2013/0002854 A1* | 1/2013 | Nielsen | H04N 7/183 348/94 |
| 2013/0176424 A1 | 7/2013 | Weil | |
| 2013/0236107 A1* | 9/2013 | Fukaya | G06K 9/46 382/201 |
| 2014/0368373 A1 | 12/2014 | Crain et al. | |
| 2015/0002638 A1* | 1/2015 | Suzuki | B60R 11/04 348/47 |
| 2015/0330911 A1 | 11/2015 | Howard | |
| 2016/0026853 A1* | 1/2016 | Wexler | H04N 5/2257 382/103 |
| 2017/0359525 A1* | 12/2017 | Weil | G01S 17/89 |

* cited by examiner

REMOTE SCANNING AND DETECTION APPARATUS AND METHOD

CROSS-REFERENCE TO RELATED APPLICATIONS

This application is a Continuation-In-Part of U.S. Ser. No. 14/708,428, filed May 11, 2015, now U.S. Pat. No. 10,104,344 issued Oct. 16, 2018, which claims the benefit of U.S. provisional patent application Ser. No. 61/992,472 filed May 13, 2014. Those applications are incorporated by reference.

BACKGROUND OF THE INVENTION (1) Field of the Invention

Disclosed herein are an apparatus and method for accurate infrared and visible spectrum scanning of an underlying terrain, detecting defects and integrating high speed acquisition and data processing of roadway and bridge subsurface and surface defects at normal highway speeds.

(2) Description of Related Art

Substantial effort, human resources, and funds are expended on a world-wide basis related to the natural and constant deterioration of roadways, bridge decks, and highway infrastructure. In particular, road surface materials such as asphalt, concrete, and reinforced concrete on bridges, decks and roadways are continuously subjected to degradation due to environmental exposure, wear, and mechanical damage caused by vehicle traffic. Constant degradation of surface materials is further enhanced by regional circumstances including and not limited to normal seasonal climatic cycles, various types of weather, high concentrations of salt-sea air in coastal areas, and exposure to de-icing salts, chlorides and developing types of de-icing chemicals in more temperate regions.

Timely, consistent and comprehensive roadway and bridge infrastructure inspection and assessment is of high importance as it relates to early detection and quantification of various types of deterioration. Without the ability to rapidly and consistently monitor the rates at which roadway and bridge deck surface material is degrading, the likelihood of further accelerated deterioration, without properly applied service and maintenance to avoid such trends, will tend to cause even further accelerated rates of deterioration.

Various methods of infrastructure inspection and assessment have been developed. Known methods range from simple visual inspection to highly complex methods that utilize various tools and electronic devices.

One traditional method involves mechanically dragging heavy steel chain across a roadway or bridge deck surface by hand or tractor. The road surface material is typically concrete in this example. Any changes in the sound that the chain produces as it is dragged along the surface are carefully observed and noted as to the particular locations and areas on the surface itself. Particular changes to the sound produced by the chain may suggest underlying material or structural defects such as, for example, structural cracks or areas of hidden delamination within the concrete. Other mechanical means related to sounding techniques also have been developed and used with varying degrees of success.

The costs and resources required to alleviate and correct rapidly accelerating rates of deterioration tend to increase and accelerate. Further, the effects of roadway and bridge deck deterioration, if left to remain unchecked, will continue to trend toward the compromised safety of motorists and vehicles. Such consequences lead to an even greater sense of urgency to remediate.

The standard civil engineering pavement technique for determining soundness of pavement is chain dragging, hammer sounding, coring and milling of the deteriorated areas. One standard specifying this technique is ASTM D 4580. Many states have their own manual such as MNDOT Concrete Pavement Rehabilitation Manual 5-694.000.

IR scanning of pavement has been evaluated and used for the past 20 years. It is documented in ASTM D4788 (Detecting Delaminations in Bridge Decks using Infrared Thermography).

GPR is documented in ASTM D6087 for evaluating asphalt covered concrete bridge decks using ground penetrating radar. Vertical GPR reflects energy from a difference in material density (reinforcing rod, void, water line, electrical conduit, etc.) which determines the depth.

These techniques collect specific information, but do not solve the unsolved problems summarized above.

Against this background, it would be desirable to identify and locate defects in road and bridge pavements using non-destructive techniques and to characterize those defects in terms of location, area, depth, volume, defect type. Further, if would be useful to be able to collect this information without closing down a road or lane while data are gathered.

Among the references considered before filing this application are: U.S. patent publication documents 2012/0173150; 2012/0218411; 2013/0176424 and U.S. Pat. Nos. 8,803,977; 7,697,727; and 4,910,592.

BRIEF SUMMARY OF THE INVENTION

Disclosed herein are an apparatus, system and method for scanning, scoping, inspecting, analyzing, locating and quantifying defects in or on numerous types of surfaces and other structures. Several aspects of this disclosure relate in one embodiment to the use of a vehicle-mounted infrared data capture camera, a high definition visible band camera, and a laser distance or range finder that allows continuous elevation measurement of the height of the respective cameras above the surface being scanned. Additionally, the system is optionally integrated with GPS hardware to ensure synergistic timing between image collection and geographic positioning. In one embodiment data from sensors associated with the vehicle-mounted devices are acquired simultaneously with a time stamp and a location stamp for accurate data fusion and correlation. To be explained later, GPR (ground-penetrating radar) and one or more lateral distance sensors are also provided. Optionally, a simultaneous trigger actuator is deployed together with a CPU.

The self-contained system apparatus configurations include variously selected and predesigned components. Once configured and assembled as a prepackaged sensor suite as installation kits, the components are readily adaptable to commercially available highway vehicles for the inspection and evaluation of roadways, bridge decks, subsurface and surface defects, and related transportation infrastructures. Preferably, the disclosed features and techniques are optionally coupled with preferably standardized and adopted federal and state departments of transportation (DOT) output analysis and reporting of the results.

Various embodiments of this disclosure provide an improved road surface and subsurface defects scanning and scoping apparatus, system, and method that are adaptable to virtually any commercially available highway vehicle, mobile equipment, or the like, for accurate and rapid collection and recordation of surface infrared and visible spectrum image data at nominal highway speeds.

This disclosure also provides significantly improved accuracy, speedy on-site integration, and rapid processing of the recorded scan data and high-definition visible band imagery. The disclosed techniques enable the operator to identify material defects in concrete roadways and bridge decks, since areas of delamination, previous patch repairs, spalling and other defects are readily identified by infrared camera data. The operator can quickly identify and reconcile defects and anomalies presented by the infrared camera data with the high-definition visible band imagery. Once the reconciliatory steps are complete, software optionally provides accurate correlation and orientation of the recorded data with respect to global positioning system (GPS) coordinates and the time stamp.

Outputs from the techniques disclosed include correlation with geographic information systems (GIS) as well as KLM file formats associated with GIS service providers such as, and not limited to for example, United States Geological Survey (USGS), or Google Earth, thus providing accurate reference to these types of three-dimensional databases.

As noted earlier, the present invention accurately and quickly identifies and quantifies various types of structural defects within roadway and bridge deck surfacing materials such as concrete and asphalt at normal and nominal traffic highway speeds. Therefore, the road surface and substructure scanning and scoping apparatus, system, and method reduces or eliminates road and traffic lane closures associated with prior methods.

For example, the methodology disclosed is suitable for scanning and scoping of airport runways and taxiways since it is mounted on commercially available highway vehicles. Applications of the disclosed method and apparatus extend to infrastructure analysis within the aviation industry including, for example, commercial, private, and military airports and facilities. The disclosed techniques can be utilized in connection with virtually any type of transportation surface and/or infrastructure.

These and other features, advantages, and objects of the present invention will be further understood and appreciated by those skilled in the art by reference to the following specification, claims, and appended drawings.

DETAILED DESCRIPTION OF THE INVENTION

Figure 1:
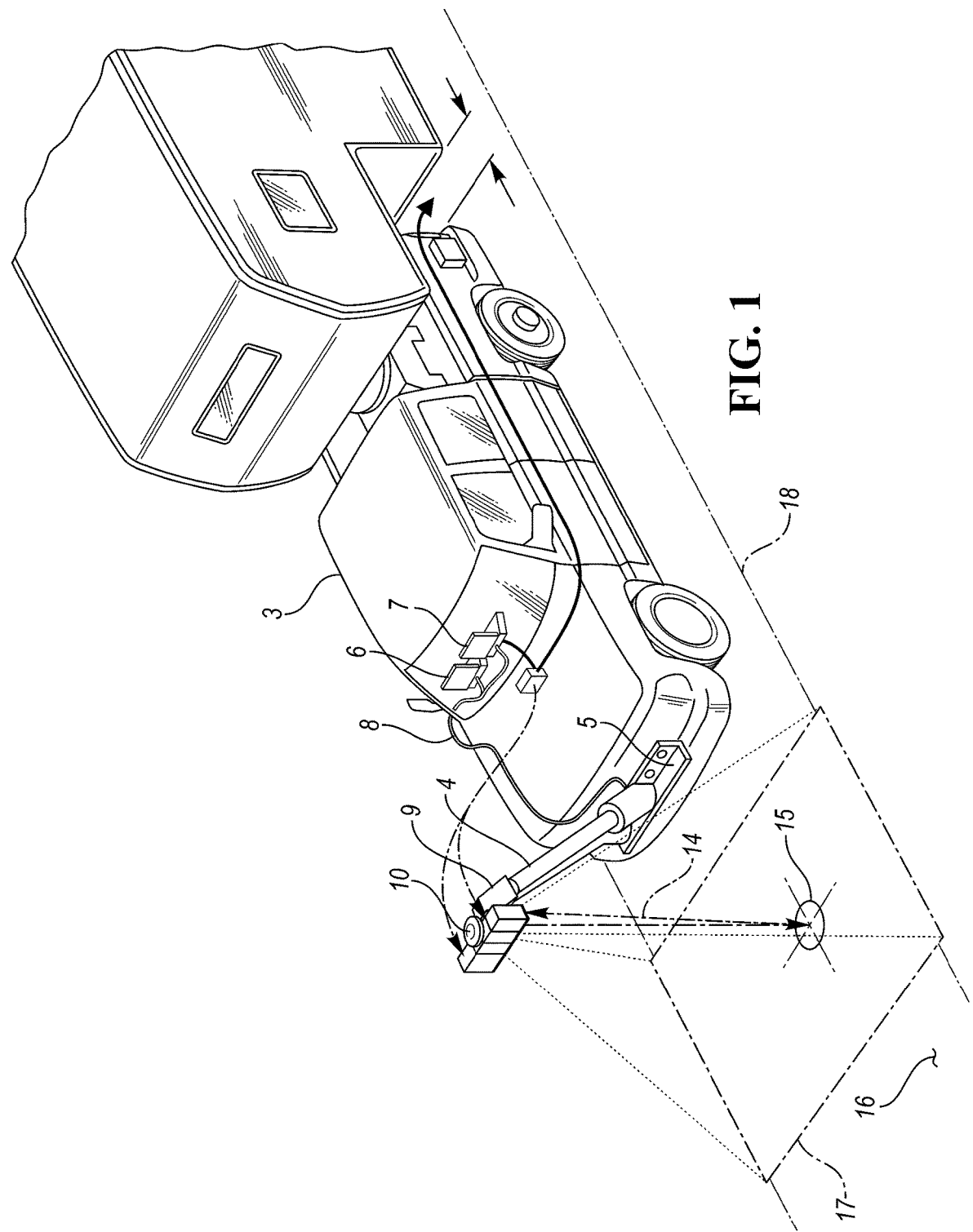
FIG. 1 is a quartering front perspective view of scanning and scoping apparatus and system embodying several features of the present invention.

FIG. 1 depicts a roadway and bridge deck scanning and scoping apparatus and system 2 embodying some features of the present disclosure—a scanning and scoping sensor head assembly 2 adaptably mounted to a commercially available highway vehicle 3 by a structural boom assembly 4. The boom assembly 4 is attached to and is preferably forwardly-mounted on the vehicle 4 by attachable brackets 5. The scanning and scoping sensors are directed generally downwardly at the roadway or bridge deck surface 16 to be scanned and scoped to prevent skewing of the edges of the frames as the vehicle 4 is driven while it travels forwardly at nominal highway speeds thereabove for recording electronic signal data from the sensors.

Figure 2:
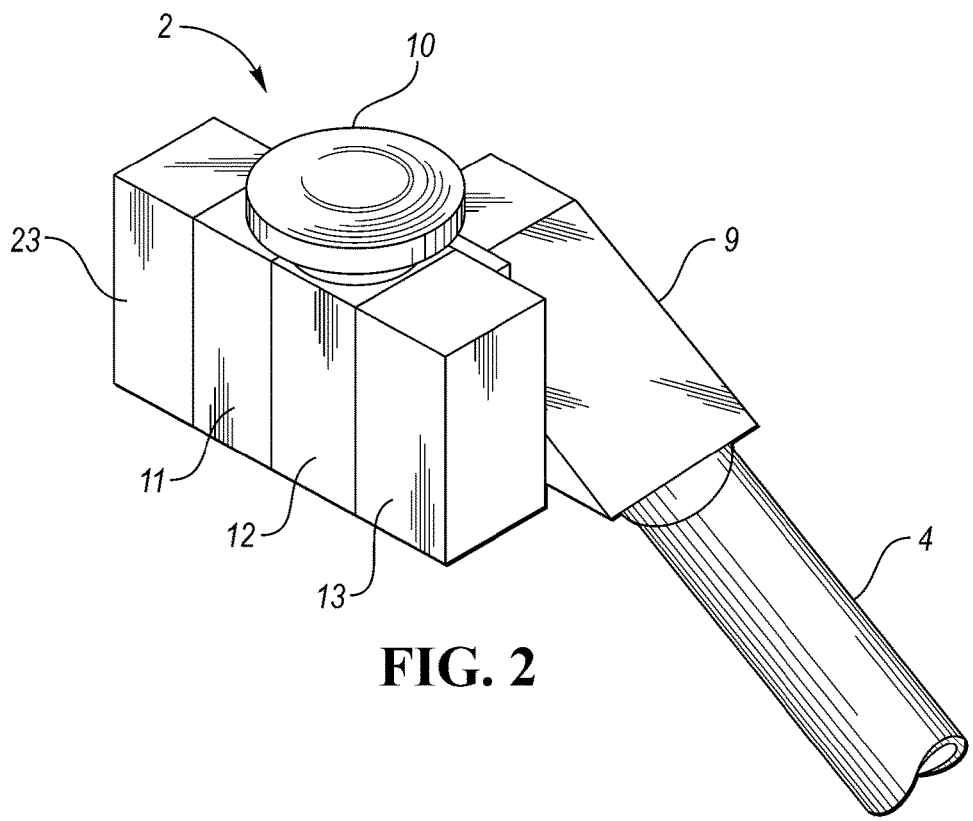
FIG. 2 is an enlarged quartering perspective view of the scanning and scoping head assembly of the present invention.
Figure 3:
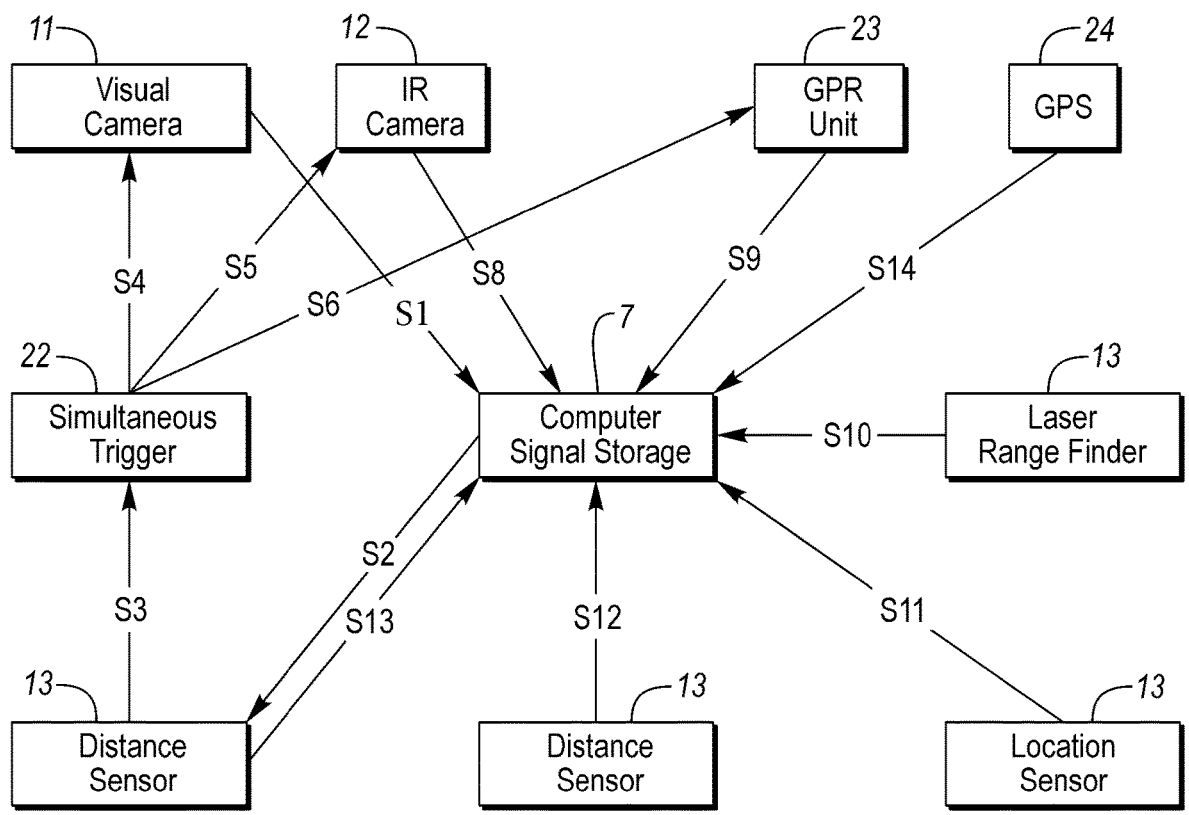
FIG. 3 is a diagram of the main components and their interactions.

FIGS. 2-3 are respectively quartering perspective views of one embodiment of the disclosed scanning and scoping head assembly 2 and a system interaction diagram. They show the general arrangement of several types of sensors— a. a high-definition visual band camera 11 for capturing images of the surface to be evaluated, b. a high-definition infrared camera 12 for sub-surface observation, c. a laser range finder 13 for accurately measuring the actual working height or elevation of the scanning and scoping head assembly above the roadway or bridge deck surface to be scanned, d. a global positioning system (GPS) antenna 24 preferably mounted at the upper portion of the scanning and scoping head assembly. The GPS locates the scanning and scoping head assembly as it remains either stationary or travels with respect to latitude, longitude and elevation (three dimension coordinates) within GPS measurement networks and geographic information systems (GIS), and e. a distance sensor 13 that detects the distance traveled by the sensor head assembly 2 from a point of origin.

The disclosed apparatus and method enable accurate and repeatable infrared and visible spectrum scanning. This allows surface and sub-surface conditions to be sensed and reported to an on-board processor. Information about roadway and bridge deck sub-structures and surface defects can be integrated and processed while the vehicle moves at normal highway speeds. Linked to or embedded within the processor is a preferably standardized and accepted DOT output analysis and method for reporting the results. More particularly, the present invention provides for a variety of generally self-contained system apparatus configurations.

The invention accurately, quickly, and reliably locates, identifies and quantifies the structural conditions and integrity of the structural materials underlying the surfaces and sub-surface structures being scanned.

In the embodiment of FIGS. 1-2 the invention the structural boom assembly 4 is preferably attached to the forward end of vehicle 3 to mechanically support the sensor head assembly 2 above the surface 16 to be scanned. It is however understood that the boom assembly 4 may optionally be adapted and attached to the rear portion of the vehicle 3. Alternatively, the boom assembly can be attached to either the left or right side portions of the vehicle 3 as may be preferred. Similarly, the sensor head assembly 2 can be mounted at alternate locations with respect to the vehicle 3, the desired direction of travel of the vehicle 3, or area to be scanned.

Bracket assembly 9 adapts and rigidly mounts the sensor head assembly 2 to the boom assembly 4. When not in use the scanning and scoping sensor head assembly 2, boom assembly 4, bracket assembly 9, attachable brackets 5 and electronic signal cable 8 may be readily detached and otherwise disassembled from the vehicle 3 to allow normal operational use and utility of the vehicle 3 as desired.

In one embodiment (FIGS. 1-2), the scanning and scoping sensor head assembly 2 has three scanning and scoping sensors 11, 12, and 13. Scanning sensor 11 comprises a visual band high-definition video camera. The camera is oriented generally vertically and receives visible band video images of the surface to be scanned 16 at scanned area 17. During this operation, the highway vehicle 3 may remain stationary or be driven forwardly.

The IR camera 12 typically is a high-definition infrared camera that is oriented vertically. It receives infrared video images of the surface to be scanned 16 at scanned area 17 as the highway vehicle 3 remains stationary or is driven forwardly.

A distance measuring sensor or distance sensors 13 may, for example, include a laser range finder, a sonic distance measuring sensor, or other similar sensors having non-contact distance measuring capability. Distance measuring sensor 13 is disposed generally adjacent to both the visible band camera 11 and infrared camera 12 and is preferably calibrated to match the elevation of both the visible band camera 11 and the infrared camera 12.

The distance measuring sensor 13 emits, for example in the case of a laser range finder a laser beam 14 onto the surface being scanned 17 at target area 15. Laser beam 14 is then reflected back to the sensing portion of laser range finder 13. The received signal is then processed electronically to provide an accurate real-time elevation distance or height measurement of the sensor head assembly 2 above the surface 16 to be scanned and scoped or the sensors' distance from a point of origin.

Turning now to FIG. 3, in one embodiment, the visual camera 11 generates a signal S1 to a computer processor 7 for analysis, storage, and later retrieval. The processor 7 generates a signal S2 which is communicated to one of the distance sensors 13. That sensor 13 delivers a signal S3 to a simultaneous triggering mechanism 22. That mechanism 22 communicates a signal S4 to the visual camera 11 which causes an image of the underlying terrain to be captured. Simultaneously, the trigger 22 sends a signal S5 to the infrared camera 12. As a consequence the IR camera 12 causes an image to be captured. That image is then communicated via signal S8 to the processor 7.

At the same time, the simultaneous trigger 22 also emits a signal S6 to the ground penetrating radar (GPR) unit 23. The GPR unit 23 captures images of the subsurface terrain and also sends these images to the processor 7 via signals S9. In the meantime, the laser range finder 13 delivers elevation information via signal S10 to the processor 7. The one or more distance sensors 13 send signals (S11, S12 and S13) that characterize distance traveled by the assembly to the processor.

Thus, there is created in the processor 7 a record, including the fields of information perhaps in tabular form described earlier which can later be retrieved and analyzed.

The GPS sensor antenna 24 is mounted preferably at the uppermost portion of the sensor head assembly 2. In this way, it may clearly receive signals from GPS satellites and other similar position tracking systems. Electronic output signals S14 generated by the GPS sensor antenna 10 are transmitted to the same computer processor 7 or a different computer processor 6 by electrical sensor and control wiring cable 8.

Optionally, each in the suite of sensors would have 6° of freedom—XYZ plus roll, pitch and yaw. Corrections to the sensors can be made real time or after the results are reported. The sensor suite generates two or more data streams—one from the GPR and one from the IR sensor.

GPR effectively defines the subsurface contours of a pothole/cavity/inclusion ("slices"). Signals from an IR sensor can define the defect's superficial footprint or perimeter. Together, IR & GPR characterize the density, dimensions, volume and shape of the defect field under observation. With mathematical modelling, from a density reading or calculation, the field can be characterized by its precise location and as a void or inclusion (e.g., a rock, granite, asphalt or concrete) of some kind.

Data fusion and analysis of signals from these sensors enable the observer to quantitatively determine for example how much concrete is needed to repair a defect.

Preferably, the sensors' field of view extends over the entire width of a road. The sweep of one or each member of the sensor suite could be controlled manually or automatically.

Under the disclosed techniques, there is no need for the vehicle to proceed at a constant speed. Observations can be made in a stop-and-go condition. The slower the vehicle, the finer is the resolution.

The system may be useful in detailing anomalies and identifying inclusions or voids based on density calculations. One example is a reinforcing bar ("Rebar"). Rebar, also known as reinforcing steel is a steel bar or mesh of steel wires used as a tension device in reinforced concrete and reinforced masonry structures to strengthen and hold the concrete in tension. Rebar can rust and become separated from (cracked) concrete. If there is no contact, the rebar is unable to support the concrete effectively. If there is corrosion, the metal rod may bind to a tube in which it is encased. The rod may no longer be able to be in tension along its entire length. Adjustment may be needed. This may be indicated by the system.

Additional features can be observed: a crown, super elevation, expansion joints, a curb and several kinds of defects: cracks—XYZ; potholes—visual & infrared plus GPR; tenting—buckles at expansion joints; rutting—where the asphalt is deformed.

To provide relevant characterizing information, extending from a moving platform (e.g., a ground-based vehicle 3) is a mounting means such as a boom 4 with a proximal end attached 5 to a moving platform (ground-based or an unmanned aeronautical vehicle—drone) and a distal end 9 that supports a suite of sensors. A controlled positioning system guides the boom's distal end 9 in the XYZ planes (left-right, in-out & vertical). In some embodiments, wireless communication is contemplated between the sensors and an onboard computer processor.

The boom 4 may extend from one or more of the vehicle's front, sides or the rear. The boom need not necessarily be at the same distance from the surface or angle during observation. One embodiment contemplates two lateral booms, each on a different side or end of the vehicle, with or without a longitudinal boom extending forwardly from the vehicle's leading edge. The lateral booms allow the pavement to be scanned simultaneously or independently on opposite sides of the vehicle.

In another embodiment, on a given side of the vehicle, the boom is lifted so that its distal end overlies terrain on the far side of a barricade. Underlying pavement can then be scoped by two sensors supported by one or two booms on opposite sides of a barricade, while the vehicle moves, providing no telephone or light poles intervene. In that case, the vehicle is stopped and the boom(s) is retracted. After sensing, the vehicle advances and the boom(s) re-extended.

Under the influence of an actuator(s), one positioning device (FIG. 3, 24) moves the distal end of the boom in response to signals that characterize the terrain ahead (pitch changes). This device 24 also provides an automatic adjustment via signal S14 of the beams generated by devices in the sensor suite at the distal end of the beam so that they impinge upon the surface below at a 90 degree angle ("perpendicularity feature"). Perpendicularity (90°) of the incident sensing beams to the surface being assessed contributes to the accuracy of information provided. In contrast, several prior art approaches project forwardly. This perpendicularity feature is effective regardless of the underlying surface or slope of the road ahead. For instance, the beam angle in relation to the boom to achieve perpendicularity is different when the vehicle moves on a non-flat surface uphill, over a crest, or downhill. Similarly for a drone's climb, descent or straight and level flight. To maintain perpendicularity, adjustments may also be made in a lateral plane if the ground-based vehicle journeys along a path that is banked.

As a result, crisp images are created. There is no fading at the edges of the pages, nor is there any blurring at the edges. This requires a narrow field of view.

GPR systems 23 work when the surface to be observed is wet and perhaps underwater. GPR uses radar that penetrates below the surface, in-depth—rather than superficial. And it provides the opportunity to generate sharply defined images. It may be slower than infrared sensors and thus require the vehicle to move more slowly.

IR and GPR data can usefully be overlaid. High resolution is provided which is better than is available from either individually. Optionally, an operator can superimpose the sensors simultaneously.

In brief, several embodiments offer the following capabilities:

A. Calculating the volume of the defect (see above)

B. Automatic painting (marking) of the defects. Precise location information is tracked by the GPS sensor antenna 24 and stored. Optionally, heads for delivering a paint spray are controlled by a processor 7 that communicates with the GPS sensor antenna 24. As a vehicle drives along it can mark the defective areas. This dispenses with the need to mark manually.

C. Translating into multiple software suites. Various municipalities have different software programs that ideally conform with federally-mandated protocols. As an operational interface, the system can generate outputs in formats that are compatible with the locally adopted software.

D. Inputting data into crack propagation or life prediction estimates. Consider a railroad bridge with holes in it. They may be small. Should they be patched now or not? If not now, when? If small, they may not be a problem. A flaw size is measured and stored as of a given point in time. Suppose it isn't big enough to warrant the cost of repair at present.

E. Comparing previous scans to determine defect growth & growth rates. Consider a situation in which the crack propagates, resulting in a bigger flaw. The situation is observed again in a couple of years. A comparison is made with the earlier observation. A model calculates the rate of propagation and reports the results. An informed decision can then be made on whether the situation justifies the repair cost.

F. Inputting data into structural integrity evaluations. Consider a bridge supported by metal beams between which lie expansion joints. The system allows observations to be made and recorded about structural integrity (load concentration and distribution) around the expansion joints.

G. Providing a visual camera 11 yields additional information about X, Y & Z locations. Snapshots (digital images) can be taken for reference and stored about surrounding environmental conditions.

H. Scanning concrete or asphalt overlays. The system can scan balconies, balustrades, walls, concrete floors of commercial buildings or parking decks for example. The surface under observation need not be horizontal.

Optional features include:

3-D System GPR. Instead of a single GPR sensor 23, an optional array of antennas is contemplated. Such sensors may be installed on a planar base, yet each could be oriented forwardly, rearwardly, or to one side or the other. Such features would then enable defects to be detected that underlie an optically opaque medium, such as rebar. Images from multiple sensors could then be stitched together in such a way as to provide images that portray the situation in three dimensions. This enables defect volumes to be calculated and be more accurately characterized.

One representative sensor supplier is 3D-Radar, part of the Chemring Group (see, www.3d-radar.com). It is expected that at any given vehicle speed, the resolution of such images is improved as compared to the resolution generated by a single sensor mounted on a vehicle driving at the same speed.

Data from an array of sensors can be fed into crack propagation models. Such approaches enable defects to be characterized (e.g. by location, size, etc.) and defined, for example, if they underlie rebar and so previously could not have been detected.

Higher Speeds. By positioning for example an IR camera 12 on the boom 4 or located at the front of a vehicle and a GPR sensor 23 at its rear, enhanced image resolution is possible, even when the vehicle travels at faster speeds. At such speeds, partial images are generated that are then stitched together to develop a complete frame in the X, Y, and Z directions.

Preferably, such images can be generated a vehicle speeds greater than 45 miles an hour. Such results would not been possible using a single GPR scanner 23. To accomplish this, the IR and GPR 12, 23 scanners emit different wavelengths. For example, the IR scanner might generate a wavelength of between about 5 and 12μ, whereas the GPR radar sensor might emit energy in the range of about 3 to 5μ.

Generally IR techniques are suited for identifying delaminations in the top layer of concrete decking (depths of 4"-6") or down the top reinforcing bar layer. GPR techniques identify the depth of the delamination.

Overall, the disclosed systems and methods (FIGS. 1-3) combine several optional features that characterize the subsurface defect. Those features include:

1. IR thermography;

2. GPR array 23 at different angles +45, 0, −45 degrees or other angles;

3. Triggering device 23 for simultaneous data collection of sensors;

4. Vehicle location sensor 13;

5. Distance measurement sensor 13;

6. Computer processor 7 for data acquisition and data fusion; and

7. Vehicle mounted spray apparatus for marking defects on the pavement.

An IR sensor 12 determines deterioration locations combined with 3-D GPR 23 to identify the 3 dimensional characteristics of the defect. This data fusion provides a 3 dimensional model of the void including volumes, even beneath a strong reflecting material such as a steel reinforcing bar. Typical vertical GPR arrangements cannot provide data beneath such barriers.

As examples of use, the disclosed methodology enables the scanning and scoping of airport runways and taxiways. Applications extend to infrastructure analysis within other facets of the aviation industry including, for example, commercial, private, and military airports and facilities and to virtually any type of transportation surface and/or infrastructure.

Embodiments of the disclosed system include selected and pre-designed components. Once configured and assembled they may be offered as prepackaged sensor suite installation kits that are readily adaptable to commercially available highway vehicles for inspection and evaluation of roadways, bridge decks, sub surface, surface defects, and related transportation infrastructures. Optionally the disclosed methodology may be used in combination with preferably standardized and adopted federal and state Departments of Transportation (DOT) systems for output analysis and reporting of the results.

The disclosed system provides significantly improved accuracy, rapid on-site integration, and rapid processing of the recorded scan data and high-definition visible band imagery. It provides the operator with the ability to identify material defects in concrete roadways and bridge decks whereby the presence of areas of delamination, previous patch repairs, spalling, and other defects are readily identified by means of infrared camera data.

Further, the operator is given the ability to quickly identify and reconcile defects and anomalies presented by the infrared camera data with the high-definition visible band imagery. Once the reconciliatory steps are complete, software may be utilized to provide accurate correlation and orientation of the recorded data with respect to global positioning system (GPS) coordinates.

The present disclosure is therefore adapted to provide output reporting including correlation with geographic information systems (GIS) as well as KLM file formats associated with GIS service providers such as, and not limited to for example, United States Geological Survey (USGS), or Google Earth, thus providing accurate reference to these types of 3-dimensional databases.

As mentioned earlier, the surface scanning apparatus can be operated at nominal highway speeds and preferably at a general magnitude of travel velocity in the range of 50 miles per hour (80 kilometers per hour). In this way, roadway lane and bridge closures, the re-routing of traffic onto alternate routes, the slowing of normal vehicle traffic, or otherwise significant interruptions to the normal and safe flow of traffic and vehicles are at least partially or entirely eliminated.

In one exemplary embodiment, the surface scanning apparatus system and kit has a vehicle-mounted high-definition visible band camera 11; a vehicle mounted high-definition infrared band camera 12; a structural boom assembly 4 attached to the highway vehicle 3 so that the high-definition visible and infrared cameras are remotely mounted at a desired elevation above the surface to be scanned to achieve a desired field of view (FOV); and a GPS 24 mounted alongside or thereabove. The field of view (FOV) to be scanned may be selected and preferably for example be approximately at least one traffic lane in width or more as a portion of the roadway or bridge deck surface.

Preferably, the structural boom assembly 4 also supports an electronic laser range finder 13 for accurately measuring the elevation height of the vehicle-mounted high-definition visible and infrared band cameras. The electronic laser range finder provides an accurate reference signal for calibration and correction factors related to the elevation height and data signals received by the vehicle-mounted high-definition visible and infrared band cameras.

As mentioned, there are one or more GPS antennas 24 for real-time recording of vehicle position, speed, and direction with respect to actual latitude and longitude coordinates (GIS and KLM files associated with Google Earth). Such signals further correlate these measurements with the measurements and data collected by the vehicle-mounted high-definition visible and infrared band cameras.

Coupled with these components are one or more computer processors 6, 7 for digitally processing the measurements and video data signals collected by the vehicle-mounted high-definition visible and infrared band cameras. The computer processors have a high-speed processor and software for rapid integration (fast high speed frame rate) of video data signals collected by the vehicle-mounted high-definition visible and infrared band cameras. In communication with the processor(s) is a digital storage device whereby recorded data and signal outputs from the means described above are stored.

Also provided are digital software programs that process the recorded data and signal outputs and formats it for output and analysis.

Preferably, the output format includes quantitative data related to the calculated percentage of structural defects and their respectively defined physical locations with respect to GPS standards in accordance with customer defined specifications, the transportation industry, and respective governing body standards.

One way to practice the disclosed techniques is to provide, not necessarily in the order listed:

a vehicle-mounted high-definition visible band camera 11;

a vehicle-mounted high-definition infrared band camera 12;

a structural boom assembly 4 attached to the vehicle whereby the high-definition visible and infrared cameras are remotely mounted at a desired elevation height above the surface to be scanned so as to encompass the desired field of view (FOV) (the FOV is preferably for example approximately at least one traffic lane in width or more as a portion of the roadway or bridge deck surface);

an electronic laser range finder 13 for accurately measuring the elevation height of the vehicle-mounted high-definition visible and infrared band cameras (the electronic laser range finder provides an accurate reference signal for calibration and correction factors related to the elevation height and data signals received by the vehicle-mounted high-definition visible and infrared band cameras);

at least one GPS antenna 24 for real-time recording of vehicle position, speed, and direction with respect to actual latitude and longitude coordinates (GIS and KLM files associated with Google Earth), further correlating these measurements to the measurements and data collected by the vehicle-mounted high-definition visible and infrared band cameras;

a computer 7 for digitally processing the measurements and video data signals collected by the vehicle-mounted high-definition visible and infrared band cameras. Optionally, the computer also runs software for rapid integration—fast high speed frame rate—of video data signals collected by the vehicle-mounted high-definition visible and infrared band cameras; and has (1) a digital storage device whereby recorded data and signal outputs from the means described above are stored; (2) digital proprietary software programs that further process the recorded data and signal outputs and formats the results for output and analysis; and (3) at least one digital output monitor that displays the output of the digital proprietary software so the operator may readily visualize the internal structural condition of the material below the surfaces previously scanned—this allows the operator to identify and locate structural defects and features apart from those cause by superficial, visible band, or non-structural defects of the scanned surfaces.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A surface and sub-surface scanning apparatus for scanning, scoping, inspecting, analyzing, locating and quantifying defects in or on numerous types of surfaces and other structure (collectively "substrate"), the apparatus being adapted to be attached to a movable highway vehicle, mobile equipment or a drone (collectively, "platform") that passes over the substrate, wherein at least some of the surface and sub-surface features of the substrate are to be sensed and characterized, the apparatus including
   a processor for receiving and processing measurements and signals from a variously adaptable, complete, and ready to operate scanning and scoping sensor head assembly including components a-e:
      a. a vertically mounted visual scanning sensor with a high-definition visible band camera for capturing surface images of a planar or undulating portion of the substrate to be evaluated, wherein the high-definition visible band camera is positioned vertically above a portion of the substrate to be scanned;
      b. a vertically mounted infra-red scanning sensor with a high-definition infra-red band camera for defining a defect's sub-surface footprint or perimeter, wherein the infra-red scanning sensor is positioned vertically above the portion of the substrate to be scanned;
      c. a 3-D ground-penetrating radar unit that is mounted at an angle between −45 degrees, vertically or +45 degrees in relation to a normal line extending from the portion of the substrate to be characterized for defining sub-surface contours of a defect in wet or dry conditions so that together the infra-red band camera and 3-D ground-penetrating radar unit are adapted to characterize the density, dimensions, volume and shape of a defect field under observation, even under a opaque barrier such as Rebar;
      d. a distance sensor for sensing distance of the apparatus from an object or from the substrate spaced apart from the apparatus, the distance sensor providing a reference signal to the processor for deriving calibration and correction factors related to height and data signals received and sent by the high-definition infra-red band camera and visible band camera;
      e. a global positioning unit for determining the position of the apparatus, the global positioning unit enabling real-time recording of vehicle position, speed, and direction with respect to actual position coordinates and ensuring synergistic timing between image collection and geographic positioning, the apparatus further having
         a structural boom assembly attached to the platform for securing and re-positioning the scanning and scoping head assembly in real time to achieve perpendicularity, the structural boom assembly also being attachable to the front, rear or side of the platform, a distal end of the structural boom assembly being adapted to move parallel to the X, Y, or Z axes, thus enabling the high-definition visible band camera and infra-red scanning sensor to scan perpendicularly in relation to the substrate and be mounted at a desired distance from the portion of the substrate to be scanned and achieve a desired field of view (FOV); and
         a simultaneous trigger mechanism that communicates with the visual band camera, the infra-red band camera, and the 3-D ground-penetrating unit so that images are captured simultaneously and communicated to the processor,
         the apparatus thereby providing improved accuracy, speedy on-site integration, and rapid processing of recorded scan data and high-definition visible band imagery, thus enabling an operator to identify material defects in concrete roadways, bridge decks, airport taxiways and runways, areas of delamination, previous patch repairs, spalling and other defects so that the operator can identify and reconcile defects and anomalies presented by the infrared camera data and the high-definition visible band imagery, so that the processor is adapted to provide accurate correlation and orientation of the recorded data with respect to global positioning system (GPS) coordinates and a time stamp.

2. The surface and sub-surface scanning apparatus of claim 1, wherein the platform is attached to a vehicle that operates at nominal highway speeds and preferably at a general magnitude of travel velocity of 50 miles per hour (80 kilometers per hour), whereby roadway lane and bridge closures, the re-routing of traffic onto alternate routes, the slowing of normal vehicle traffic, or otherwise significant interruptions to the normal and safe flow of traffic and vehicles are at least partially or entirely eliminated.

3. The surface and sub-surface scanning apparatus system of claim 1, wherein the distance sensor provides an accurate reference signal for calibration and correction factors related to the height and data signals received by either or both of the vehicle-mounted high-definition visible and infra-red band cameras.

4. The surface and sub-surface scanning apparatus of claim 1, wherein the processor includes a computer for receiving, storing and processing measurements and video data signals collected by the high-definition visible and infra-red band cameras.

5. The surface and sub-surface scanning apparatus system of claim 4, wherein the computer further includes a high-speed processor and software for integration of video data signals collected by the high-definition visible and infra-red band cameras.

6. The surface and sub-surface scanning apparatus system of claim 5, wherein the computer and high-speed processor further include a digital storage device whereby recorded data and signal outputs are stored.

7. The surface and sub-surface scanning apparatus system of claim 6, wherein the computer and high-speed processor further include digital software programs whereby the recorded data and signal outputs are further processed and formatted for output and analysis.

8. The surface and sub-surface scanning apparatus system of claim 7, further including at least one monitor for displaying the output so that the operator may visualize an internal structural condition of material below the substrate scanned, thus allowing the operator to identify and locate sub-surface structural defects and features apart from superficial or nonstructural defects of the scanned substrate.

9. The surface and sub-surface scanning apparatus system of claim 8, wherein the processor generates an output format consistent with quantitative data related to a calculated percentage of structural defects and their respectively defined physical locations with respect to GPS standards in accordance with customer-defined specifications, the transportation industry, and/or respective governing body standards.

10. A method for evaluating surface and sub-surface conditions of a substrate, the method comprising at least some of the steps of providing, not necessarily in the order listed
   a processor for receiving and processing measurements and signals from the group of components (a.-e) of claim 1; and
   a structural boom assembly having a distal end that is movable about the X, Y, Z axes and a proximal end that is attachable to the front, rear or a side of a platform whereby the high-definition visible and infra-red cameras and the surface penetrating radar unit are remotely mounted on a platform at a desired distance from the surface to be scanned so as to encompass a desired field of view (FOV).

11. The surface and sub-surface scanning apparatus of claim 1, further including:
   one or more heads for delivering a paint spray that are controlled by the processor so that as the platform moves, the platform can mark the substrate at or above the surface and sub-surface defective areas, thus dispensing with a need to mark manually.

12. The surface and sub-surface scanning apparatus of claim 1, where the components of the scanning and scoping sensor head assembly have six degrees of freedom that include displacement of the scanning and scoping sensor head assembly parallel to X, Y, and Z axes and roll, pitch and yaw motion.

* * * * *